United States Patent [19]

Schwartz et al.

[11] Patent Number: 5,073,498
[45] Date of Patent: Dec. 17, 1991

[54] FLUORESCENT ALIGNMENT MICROBEADS WITH BROAD EXCITATION AND EMISSION SPECTRA AND ITS USE

[75] Inventors: Abraham Schwartz; Emma F. Repollet, both of Hato Rey, P.R.

[73] Assignee: Caribbean Microparticles Corporation, Hato Rey, P.R.

[21] Appl. No.: 494,975

[22] Filed: Mar. 16, 1990

Related U.S. Application Data

[63] Continuation-in-part of Ser. No. 465,792, Jan. 16, 1990, which is a continuation-in-part of Ser. No. 374,435, Jun. 30, 1989, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^5$ .............. G01N 21/00; G01N 31/00
[52] U.S. Cl. ..................................... 436/8; 436/10; 436/63; 436/800; 436/808; 435/967
[58] Field of Search ........................ 436/8–18

[56] References Cited

U.S. PATENT DOCUMENTS

| | | | |
|---|---|---|---|
| 4,035,316 | 7/1977 | Yen | 260/2.5 |
| 4,157,323 | 6/1979 | Yen | 260/29.7 |
| 4,162,282 | 7/1979 | Fulwyler et al. | 436/10 |
| 4,247,434 | 1/1981 | Vanderhoff | 260/29.6 |
| 4,254,096 | 3/1981 | Monthony | 424/8 |
| 4,438,239 | 3/1984 | Rembaum | 525/54.1 |
| 4,511,662 | 4/1985 | Baran | 436/513 |
| 4,552,633 | 11/1985 | Kumakura | 204/159 |
| 4,605,630 | 8/1986 | Kung | 436/511 |
| 4,609,689 | 9/1986 | Schwartz | 523/202 |
| 4,656,144 | 4/1987 | Hosaka | 436/534 |
| 4,665,020 | 5/1987 | Saunders | 405/7 |
| 4,694,035 | 9/1987 | Kasai | 524/458 |
| 4,698,262 | 10/1987 | Schwartz | 428/402 |
| 4,699,826 | 10/1987 | Schwartz | 428/402 |
| 4,699,828 | 10/1987 | Schwartz | 428/402 |
| 4,714,682 | 12/1987 | Schwartz | 436/10 |
| 4,751,188 | 6/1988 | Valet | 436/63 |
| 4,767,206 | 8/1988 | Schwartz | 436/10 |
| 4,774,189 | 9/1988 | Schwartz | 436/10 |
| 4,828,984 | 5/1989 | Schwartz | 435/7 |
| 4,857,451 | 8/1989 | Schwartz | 436/10 |
| 4,868,126 | 9/1989 | Schwartz | 436/19 |
| 4,918,004 | 4/1990 | Schwartz | 436/10 |

*Primary Examiner*—David L. Lacey
*Assistant Examiner*—William Chan
*Attorney, Agent, or Firm*—Olive & Olive

[57] ABSTRACT

Highly uniform microbeads containing a single fluorescence dye or a mixture of fluorescence dyes, which can be excited over a wide range of the spectrum extending from the ultraviolet to the infrared, and which can be used to align a flow cytometer or fluorescence microscope.

12 Claims, 2 Drawing Sheets

FLUORESCENT ALIGNMENT MICROBEADS WITH BROAD EXCITATION AND EMISSION SPECTRA AND ITS USE

CROSS-REFERENCE TO RELATED APPLICATIONS

This application is a continuation-in-part of U.S. application Ser. No. 07/465,792 filed 1-16-90, which is a continuation-in-part of U.S. application Ser. No. 07/374,435 filed June 30, 1989; which is a continuation-in-part of U.S. application Ser. No. 07/128,786 filed Dec. 4, 1987, issued Aug. 15, 1989 as U.S. Pat. No. 4,857,451; which is a continuation-in-part of U.S. application Serial No. 06/805,654 filed Dec. 11, 1985, issued Sept. 27, 1988 as U.S. Pat. No. 4,774,189, which in turn is a continuation-in-part of U.S. application Ser. No. 06/685,464 filed Dec. 24, 1984, issued Aug. 30, 1988 as U.S. Pat. No. 4,767,206.

BACKGROUND OF THE INVENTION

1. Field of the Invention

This invention relates to fluorescent microbeads used to align fluorescent microscopes and flow cytometers, and in particular, relates to highly uniformly sized fluorescent microbeads which fluoresce over a wide range of excitation and emission wavelengths.

2. Description of the Related Art

Flow cytometers are used to analyze biological cells and particles present in a fluid sample by intersecting a thin stream of the fluid by an illumination source, usually a laser beam. The resulting forward and right angle scattered and fluorescent light is analyzed with photomultiplier tubes (PMTs). The fluorescent channels of a flow cytometer, designated by F11, F12, F13 etc., are each set with barrier filters to detect a selected specific dye while filtering out signals from dyes that fluoresce at other wavelengths.

Fluorescence instruments such as flow cytometers and fluorescence microscopes require alignment of their optical components for optimal performance. This alignment involves obtaining the most intense fluorescence signal from the instrument. More specifically in the case of flow cytometers, alignment requires obtaining the tightest grouping of events (lowest percent coefficient of variation, % CV) on the two dimensional dot plots of the fluorescence channels FL1 and FL2 as shown by comparison of the dot plots of FIG. 1 (an unaligned instrument) and FIG. 2 (an aligned instrument). This is accomplished by adjusting and focusing the optical and electrical components of the flow cytometer including the laser, lenses, mirrors, barrier filters and PMTs, so that scatter and fluorescence signals have the lowest CV.

Various excitation sources may be employed by fluorescence instruments as described by H. M. Shapiro in his book *Practical Flow Cytometry*, published by A. R. Liss, 1985. These excitation sources include: mercury arc lamps which have strong emission lines at 313, 334, 365, 405, 436, 546, and 577 nm; various lasers obtainable from an argon laser with excitation lines at 457, 465, 472, 476, 488, 496, 501 and 515 nm; from a helium-cadmium laser at 325 and 441 nm; and from a krypton laser at 337, 350, 406, 413, 422,520, 530, 568, 647, 676, 752, and 79 nm. Moreover, dye pumped laser can be tuned to any specific excitation wavelength across the spectrum from the UV to IR.

Usually each configuration of a fluorescence instrument requires a specific fluorescent microbead with which to align it. Instruments using a UV excitation would require a microbead which contains a dye that excites with UV radiation, whereas an instrument that uses a helium-neon laser with an excitation line at 633 nm will need a microbead that excites with red radiation.

During the past ten years, the technology required to synthesize highly uniform microbeads in the size range of 2–20 u in diameter has been developed, both in space (for example, U.S. Pat. No. 4,247,434) and on earth (for example, U.S. Pat. Nos. 4,247,434; 4,336,173; and 4,157,323). These patents, and all other patents, applications and publications cited herein, are hereby incorporated by reference.

The technology for the use of fluorescence dyes, which have very specific and limited ranges of excitation (absorption) and emission, has also been developed and improved for incorporation of the fluorescent dyes within the body and on the surface of the microbeads. In co-pending application Ser. No. 07/465,792, microbeads multiply-labeled with specific dyes were used for adjustment of a flow cytometer in multiple fluorescent channels of the flow cytometer, for subsequent measurement of a selected sample comprising cells or particles labeled with fluorescent dyes. Thus, these previous microbeads may be used to adjust multiple channels of a flow cytometer, with each microbead having the specific dyes associated with it to match a particular sample.

It is therefore an object of this invention to provide a means of aligning flow cytometers and fluorescence microscopes for use with a wide range of wavelengths, employing microbeads which fluoresce over a wide range of excitation and emission wavelengths.

It is a further object of this invention to provide a population of microbeads which fluoresce over a wide range of excitation and emission wavelengths.

Other objects and advantages will be more fully apparent from the following disclosure and appended claims.

SUMMARY OF THE INVENTION

The invention comprises the composition, and method of synthesis of highly uniformly sized microbeads which are associated with a single or combination of multiple fluorescent dyes which will excite over a wide range of wavelengths (UV to IR) such that a variety of different laser lines or excitation bands may be used to align the fluorescence instrument with a single population of microbeads.

Preferably, the microbead population for alignment of a flow cytometer or fluorescence microscope comprises microbeads which are highly uniform in size, having a coefficient of variation of less than 2% in diameter; said microbeads containing a plurality of fluorescent dyes; said microbeads fluorescing over a wide range of excitation wavelengths; said microbeads having a fluorescence signal distribution with a coefficient of variation of less than 4%.

These microbeads preferably are made of a hydrophobic material and contain fluorescent dyes which excite over a range of wavelengths from 350 to 700 nm. The procedure for making the microbeads preferably comprises a swelling process in which a monomer is employed; wherein one or more hydrophobic fluorescent dyes is dissolved in a monomer initiator solution prior to addition of the monomer initiator solution to the microbeads for swelling and polymerization.

Other aspects and features of the invention will be more fully apparent from the following disclosure and appended claims.

DETAILED DESCRIPTION OF THE INVENTION AND PREFERRED EMBODIMENTS THEREOF

Figure 1:
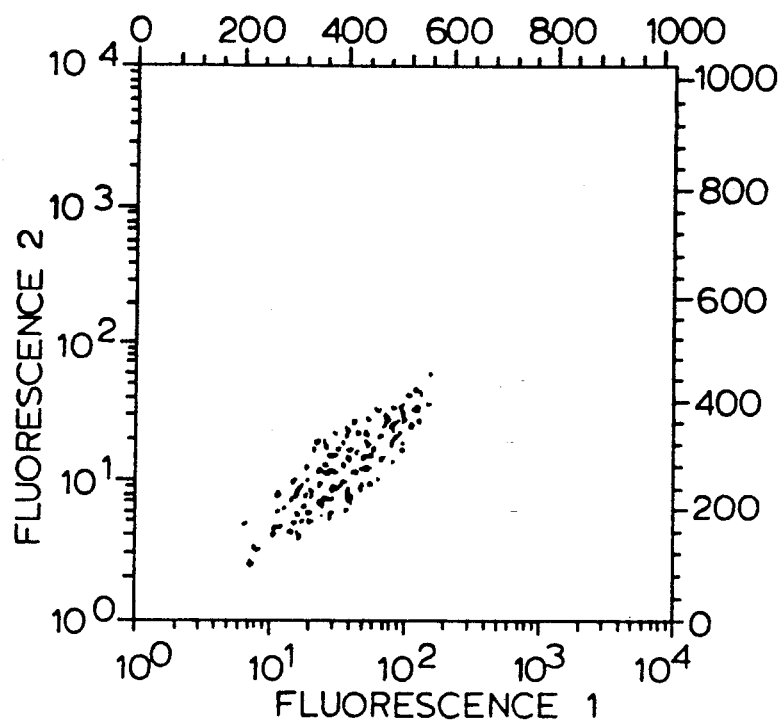
FIG. 1 is a dot plot of the FL1 versus the FL2 fluorescence channels of a flow cytometer which is out of alignment.
Figure 2:
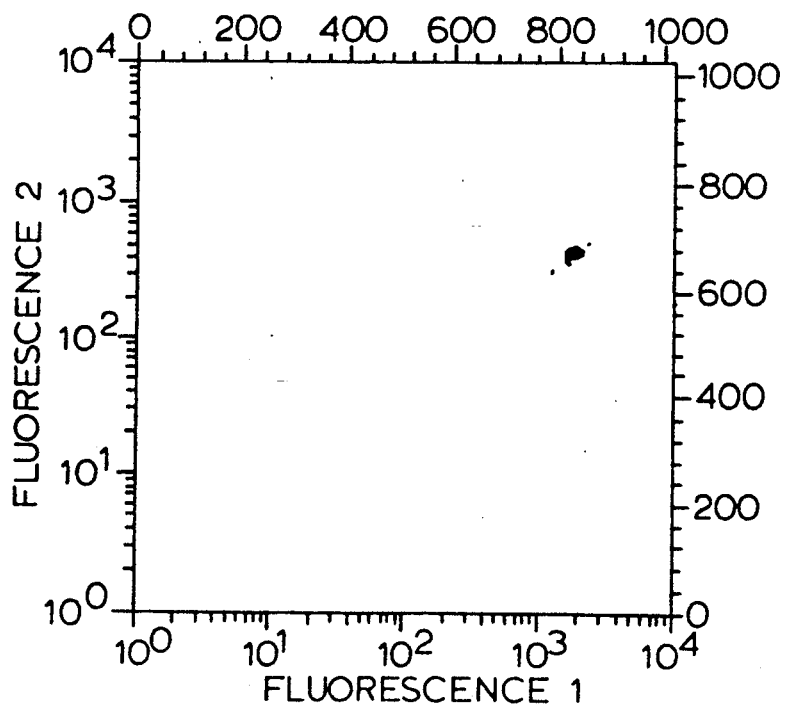
FIG. 2 is a dot plot of the FL1 versus the FL2 fluorescence channels of a flow cytometer which is optimally aligned.

The present invention includes a microbead composition, and a method of synthesis of highly uniform microbeads, each of which has a broad excitation and emission spectrum. The microbeads are preferably synthesized according to an improvement of the patents of Schwartz (U.S. Pat. Nos. 4,714,682; 4,767,206; and 4,774,189).

The microbeads of the invention for use in aligning a flow cytometer or fluorescence microscope, thus may be prepared as follows:

(a) preswelling small microbeads;
(b) dissolving one or more hydrophobic fluorescent dyes in a monomer initiator solution;
(c) adding the monomer initiator solution to the preswollen microbeads for further swelling; and
(d) polymerizing the microbeads.

Thus, during the synthesis process, the microbeads incorporate one or more fluorescent dyes, which when associated with the microbeads result in microbeads which fluoresce over a wide range of excitation and emission wavelengths. Although the fluorescent dyes may be covalently bound to the surface of microbeads or diffused into the body of the microbeads via solvent manipulation using microbeads that have been previously made, as described in the aforementioned patent, in order to obtain the most uniform fluorescence signals from the microbeads, the dyes are dissolved in the monomers and initiator solution prior to swelling and polymerization to form the microbeads. This insures that the dyes are uniformly distributed throughout the body of the microbead when it polymerizes.

When these microbeads are used with a fluorescence microscope, any excitation band from 300 to 750 nm can be used and the optics aligned such that all areas of the field of view have the maximum uniform intensity.

Microbeads excitable across the spectrum from UV to IR with CVs of less than 4% in their forward scatter and fluorescence distributions can be made by dissolving a mixture of hydrophobic dyes in the monomer initiator solutions described in the aforementioned patents.

When these microbeads are used with a flow cytometer, 356, 466, 515 and 613 nm laser lines can be used to excite the microbeads when they are used to align the optics to obtain the maximum intensity with the lowest % CV of the dot plot.

The features and advantages of the present invention will be more clearly understood by reference to the following examples, which are not to be construed as limiting the invention.

EXAMPLE I: Preparation of Microbeads of the Invention

A population of microbeads having a diameter of 2.0 microns and prepared as disclosed in U.S. Pat. Nos. 4,714,682; 4,767,206; and 4,774,189 were pre-swelled with 1-chlorodecane and then subsequently swollen with a solution of 10 mg each of Coumarin 487, Coumarin 525, Oxazine 1 (Polyscience Incorporated, Warrington, Penna.) dissolved in 50 ml methyl methacrylate (Aldrich Chemical Co., Inc., St. Louis, Mo.) containing 1.5% benzoyl peroxide. Polymerization was complete after heating to 70° C. for one hour forming a population of uniform microbeads 7.5 u in diameter (less than 2% CV in diameter). When excited with a long wavelength UV lamp, this population of microbeads fluoresced white, indicating that all wavelengths of the visible spectrum were present in the emission.

EXAMPLE II: Observation of Microbeads

When the microbeads of Example I were observed under a Labophote Nikon fluorescence microscope using UV excitation (365 nm), they appeared blue. Use of blue excitation (485 nm) resulted in the microbeads appearing yellow, and when green excitation (520 nm) was used they appeared red. This indicates that the microbead population could be used to align the microscope at any of the above wavelengths.

EXAMPLE III: Use of the Microbeads on a Flow Cytometer

Figure 3:
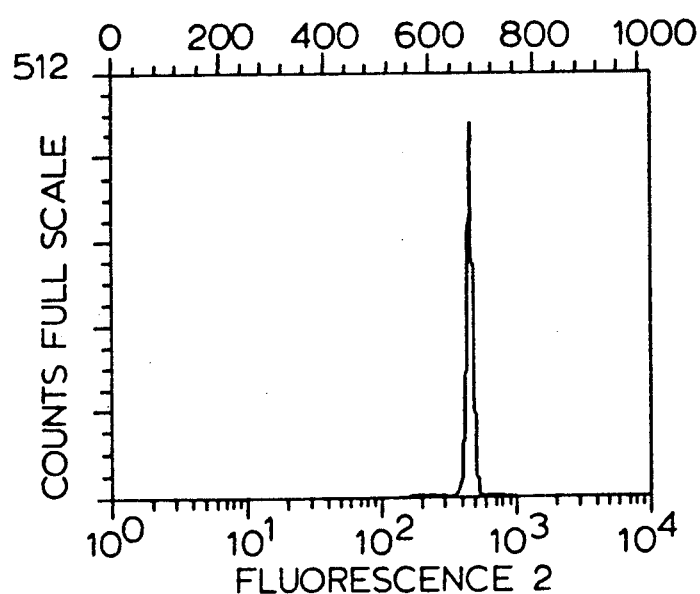
FIG. 3 is a FL2 histogram of highly uniform microbeads (less than 4% CV) from an optimally aligned flow cytometer.

When the microbeads of Example I were run on a flow cytometer using a 488 nm laser line for excitation, a tight intense dot pattern (3.5% CV for FL1 and 3.6% CV for FL2) was obtained (FIG. 3). Similar dot patterns were obtained using a 363 nm laser line for excitation.

EXAMPLE IV: Synthesis of Microbeads According to the Invention

Microbeads were synthesized as in Example I, but using Hoechst 33342, rhodamine 101, and acridine orange (Sigma Chemical Co., St. Louis, Mo.) as the fluorescent dyes. The resulting population of microbeads also fluoresced white when excited by a long wavelength UV lamp, indicating a full spectrum emission.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A microbead population for alignment of a flow cytometer or fluorescence microscope, comprising microbeads which are highly uniform in size, said microbeads having a coefficient of variation of less than 2% in diameter; each of said microbeads containing one or more fluorescent dyes so that each of said microbeads fluoresces over a wide range of excitation wavelengths and fluoresces white under a long wavelength ultraviolet lamp; said dyes selected form the group consisting of (a) coumarin 487, coumarin 525, and oxazine 1; and (b) Hoechst 33342, rhodamine 101 and acridine orange;

said microbeads having a fluorescence signal distribution with a coefficient of variation of less than 4%, wherein said microbeads may be used to align lasers at a plurality of wavelengths.

2. A microbead population according to claim 1, wherein the microbeads are formed by polymerization, and the dyes are uniformly distributed throughout the body of the microbeads during polymerization.

3. A microbead population according to claim 1, wherein the dyes are covalently bound to the microbeads.

4. A microbead population according to claim 1, wherein the dyes are intercalated into the microbeads by manipulation of a solvent.

5. A microbead population according to claim 1, wherein the microbeads are made of a hydrophobic material and contain fluorescent dyes which excite over a range of wavelengths from 350 to 700 nm.

6. A microbead population according to claim 1, wherein the microbeads contain fluorescent dyes which excite over a range of wavelengths from 350 to 700 nm.

7. A microbead population according to claim 1, wherein the microbeads are made of a hydrophobic material and are formed in a swelling process in which a monomer is employed; wherein said fluorescent dyes dissolve in a monomer initiator solution prior to addition of the monomer initiator solution to the microbeads for swelling and polymerization.

8. A microbead population according to claim 1, wherein the microbeads are methyl methacrylate and the fluorescent dyes are coumarin 487, coumarin 525 and oxazine 1.

9. A microbead population according to claim 1, wherein the microbeads are styrene and the fluorescent dyes are coumarin 487, coumarin 525 and oxazine 1.

10. A microbead population according to claim 1, wherein the microbeads are methyl methacrylate and the fluorescent dyes are Hoechst 33342, acridine orange and rhodamine 101.

11. A microbead population according to claim 1, wherein the microbeads are styrene and the fluorescent dyes are Hoechst 33342, acridine organe and rhodamine 101.

12. A method of aligning a microscope having lasers at a plurality of wavelengths, comprising utilizing microbeads which fluoresce white under a long wavelength ultraviolet lamp, said microbeads being highly uniform in size, said microbeads having a coefficient of variation of less than 2% in diameter; each of said microbeads continuing one or more fluorescent dyes, fluorescing over a wide range of excitation wavelengths, and having a fluorescence signal distribution with a coefficient of variation of less than 4%, said dyes selected from the group consisting of (a) coumarin 487, coumarin 525, and oxazine 1; and (b) Hoechst 33342, rhodamine 101 and acridine orange.

* * * * *